US007187976B2

(12) United States Patent
Duncan et al.

(10) Patent No.: US 7,187,976 B2
(45) Date of Patent: Mar. 6, 2007

(54) MULTI-PURPOSE FES SYSTEM

(75) Inventors: Michael Duncan, Lane Cove (AU); Ian Bruinsma, Lane Cove (AU); Zoran Milijasevic, Lane Cove (AU); Andrew Barriskill, Lane Cove (AU)

(73) Assignee: Neopraxis Pty Ltd., Lane Cove (AU)

( * ) Notice: Subject to any disclaimer, the term of this patent is extended or adjusted under 35 U.S.C. 154(b) by 521 days.

(21) Appl. No.: 10/346,072

(22) Filed: Jan. 17, 2003

(65) Prior Publication Data
US 2003/0181956 A1    Sep. 25, 2003

(30) Foreign Application Priority Data
Jan. 21, 2002    (AU)    ................. PS0069

(51) Int. Cl.
*A61N 1/32* (2006.01)

(52) U.S. Cl. ................. 607/43; 607/2; 607/48
(58) Field of Classification Search ............ 607/39–41, 607/48, 49, 60
See application file for complete search history.

(56) References Cited

U.S. PATENT DOCUMENTS

| 3,585,707 | A | 6/1971 | Stevens |
| 4,428,377 | A | 1/1984 | Zollner et al. |
| 4,459,989 | A | 7/1984 | Borkan |
| 4,528,984 | A | 7/1985 | Morawetz et al. |
| 4,628,934 | A | 12/1986 | Pohndorf et al. |
| 4,835,853 | A | 6/1989 | Hirschberg |
| 4,886,064 | A | 12/1989 | Strandberg |
| 4,934,368 | A | 6/1990 | Lynch |
| 5,038,781 | A | 8/1991 | Lynch |
| 5,081,989 | A | 1/1992 | Graupe et al. |
| 5,167,229 | A | 12/1992 | Peckham et al. |
| 5,193,539 | A | 3/1993 | Schulman et al. |
| 5,324,316 | A | 6/1994 | Schulman et al. |
| 5,411,535 | A | 5/1995 | Fujii et al. |

(Continued)

FOREIGN PATENT DOCUMENTS

DE    196 32 705 A1    2/1998

(Continued)

OTHER PUBLICATIONS

PCT/AU2003/000043 International Search Report, Jun. 19, 2003.

(Continued)

*Primary Examiner*—Carl Layno
(74) *Attorney, Agent, or Firm*—Jagtiani + Guttag

(57) ABSTRACT

A multi-purpose FES system includes a multi-function, implantable stimulator for stimulating different sites in a patient's body. The stimulator includes a control unit and a receiving device. The stimulator further has a plurality of bundles of electric leads connected to the control unit, each lead terminating in at least one electrode to provide a plurality of discrete groups of electrodes associated with each site. Each group of electrodes is operable to stimulate its associated site in the patient's body, under the action of stimulation signals from the control unit, the control unit receiving signals from the receiving device. A transmitter is arranged externally of the patient's body for supplying signals transcutaneously to the receiving device of the stimulator. A controller is in communication with the transmitter via a communications interface unit.

30 Claims, 16 Drawing Sheets

U.S. PATENT DOCUMENTS

| | | |
|---|---|---|
| 5,522,865 A | 6/1996 | Schulman et al. |
| 5,562,715 A | 10/1996 | Czura et al. |
| 5,776,171 A | 7/1998 | Peckham et al. |
| 5,782,841 A * | 7/1998 | Ritz et al. .................. 606/129 |
| 5,814,089 A | 9/1998 | Stokes et al. |
| 5,814,093 A | 9/1998 | Stein |
| 5,843,142 A * | 12/1998 | Sultan ........................ 607/49 |
| 5,893,881 A * | 4/1999 | Elsberry et al. ............... 607/5 |
| 5,895,414 A | 4/1999 | Sanchez-Zambrano |
| 5,987,352 A * | 11/1999 | Klein et al. ................. 600/509 |
| 6,058,326 A | 5/2000 | Hess et al. |
| 6,141,588 A | 10/2000 | Cox et al. |
| 6,163,725 A * | 12/2000 | Peckham et al. ............. 607/61 |
| 6,164,284 A | 12/2000 | Schulman et al. |
| 6,213,995 B1 | 4/2001 | Steen et al. |
| 6,272,382 B1 | 8/2001 | Faltys et al. |
| 6,315,721 B2 | 11/2001 | Schulman et al. |
| 6,622,048 B1 * | 9/2003 | Mann et al. .................. 607/46 |
| 2001/0000187 A1 | 4/2001 | Peckham et al. |

FOREIGN PATENT DOCUMENTS

| | | |
|---|---|---|
| EP | 0 165 049 A2 | 12/1985 |
| GB | 2092004 | 8/1982 |
| WO | WO 83/04182 | 12/1983 |
| WO | WO 95/10323 | 4/1995 |

OTHER PUBLICATIONS

PCT/AU2003/000139 International Search Report, May 12, 2003.

* cited by examiner

MULTI-PURPOSE FES SYSTEM

FIELD OF THE INVENTION

The present invention relates to a Functional Electrical Stimulation (FES) system. More particularly, the present invention relates to a multi-purpose FES system capable of assisting in restoration of multiple bodily functions to a patient suffering trauma to the spinal cord.

BACKGROUND OF THE INVENTION

Neurological impairment, such as spinal cord injury (SCI), can occur in people of any age, and is often caused by injuries sustained in accidents associated with motor vehicles, firearms, sports injuries, and the like. Many of the individuals who sustain such injuries are young male adults between the ages of 16 and 30 who, up to the point of the accident, have lead active and healthy lives.

In the USA, the prevalence of neurological impairment resulting from SCI is estimated at between 712 and 906 per million with the incidence of SCI being calculated at between 30 and 40 per million. It is widely recognised that SCI has a large impact on society in general and is a sudden and irreversible change, to an individual's quality of life.

In order to define SCI, it should be understood that an SCI is a traumatic lesion to the spinal cord and the associated nerves. Thirty-one spinal nerves originate from the spinal cord and can be grouped as follows: 8 cervical (C1 to C8), 12 thoracic (T1 to T12), 5 lumbar (L1 to L5), 5 Sacral (S1 to S5) and 1 coccygeal. An injury to the spinal cord can result in varying degrees of impairment depending on where and to what extent the spinal cord is injured. In general, the higher up on the spinal cord the injury, the more severe the resulting impairment.

People suffering from a SCI are essentially categorised into two main groups: tetraplegics and paraplegics.

Tetraplegics are individuals who have sustained injury to one of the eight cervical segments of the spinal cord, C1 to C8. Such an injury results in impaired use of the arms and hands as well as the legs. A person who has suffered such an injury generally experiences significant loss of sensation and volitional body movement as well as the loss of volitional bladder and bowel control. Many tetraplegics may also have loss of psychogenic and impaired reflex erections.

Paraplegics are individuals who have sustained an injury at the thoracic level, T1 to T12. These individuals usually have sensation and volitional control over their upper limbs, but have lost sensation and control of their lower limbs and bladder and bowel control, as well as erection problems in males.

Due to SCI individuals being unable to control bladder function, individuals must regularly self cathertise. This procedure is problematic, especially for females, and can result in an increase in the incidence of urinary tract infections. Still further, persons suffering from SCI must often undertake lengthy bowel evacuation procedures using, for instance, digital evacuation. SCI patients are also prone to secondary medical problems, such as pressure sores, osteoporosis, muscular atrophy in the lower limbs, muscle spasticity, deep vein thrombosis, cardiovascular disease and depression. Pressure sores are caused by the occlusion of blood flow during sitting and lying and are a major health problem which may require surgery to repair and months of rehabilitation including requiring the patient to remain lying on their abdomen for an extended period of time.

Therefore, whilst restoration of bladder and bowel control is a primary need of SCI individuals, reduced incidence of pressure sores is also highly needed. This, together with the ability to exercise and stand and step, are functions that would greatly improve the quality of life of SCI individuals.

It is therefore evident that a large proportion of the population who have a SCI would benefit from a device that would be able to assist in, at least, the partial restoration of such lost functionality, in particular bowel and bladder function, erectile function, the reduction in the incidence of pressure sores and the provision of exercise and upright mobility. Various systems have been proposed by numerous organisations to deal with one or other of the functions that have been lost to SCI individuals.

There have been systems designed for bladder control via an implantable device that have met with variable success with the majority of such devices requiring invasive surgical procedures such as posterior sacral rhizotomies and sacral laminectomies. The "Vocare" device manufactured by Finetech Medical Limited (UK) requires a posterior sacral rhizotomy and a laminectomy, in order to achieve a non-reflexive bladder with adequate capacity, and also requires a sacral laminectomy to access the anterior sacral roots to enable the cuff type electrodes to be fitted. This surgical procedure eliminates reflex erection in male recipients and it is considered that an individual who receives a rhizotomy but does not use the device would be expected to have reduced bowel activity.

There have been a number of systems proposed to assist in limb control, particularly lower limb control. The majority of such systems, such as the "Parastep" system from Sigmedics (Wheeling, Ill., USA), rely upon surface stimulation techniques that use external electrodes placed on the user's limbs to stimulate the muscles via an electric charge through the skin. Such systems are limited with regard to the functionality they can restore to the limbs due to the non-specific way that stimulation is applied. Implantable systems have also been proposed to control limb movements directly. These systems use a plurality of electrodes to stimulate targeted muscle groups, either in the lower limbs or in the arms/hands.

It will be appreciated that SCI results in loss of control over multiple physiological systems, and implants to date have only been developed to restore individual functions. A need therefore exists to provide a generic implantable stimulator capable of restoring multiple functions to an SCI individual and the stimulator being controllable by various functions or modes that are matched to an individual patient's requirements. There is also a need to provide a generic FES implant that requires less invasive surgical procedures, and only one source of control rather than multiple sources.

SUMMARY OF THE INVENTION

According to the invention, there is provided a multi-purpose FES system, the system including:

a multi-function, implantable stimulator for stimulating different sites in a patient's body, the stimulator including a control unit and a receiving device and the stimulator further having a plurality of bundles of electric leads connected to the control unit, each lead terminating in at least one electrode to provide a plurality of discrete groups of electrodes associated with each site, each group of electrodes being operable to stimulate its associated site in the patient's body, under the action of stimulation signals from the control unit, the control unit receiving signals from the receiving device;

a transmitter arranged externally of the patient's body for supplying signals transcutaneously to the receiving device of the stimulator; and a controller in communication with the transmitter via a communications interface unit.

The electrodes associated with each stimulation site may also operate as sense electrodes capable of sensing the neural response of nerves at the stimulation site to applied stimulation. In this regard, the implantable stimulator is able to store and transmit such neural response information to the external controller unit, with the receiving device then acting as a transmitter device and the transmitter acting as a receiver.

In such an arrangement, the external controller is able to sense the effect of applied stimulation to the stimulation site and record such activity to assist in understanding the parameters associated with the stimulation. Such information can be used by a clinician to customise the stimulation applied by the electrodes to optimally produce a desired effect.

The stimulator may be configured to effect stimulation of at least four sites of the patient's body. The at least four sites may include a posterior and anterior right lower extremity, a posterior and anterior left lower extremity, a posterior, sacral region of a spinal cord of the patient and at a conus of the patient's spinal cord.

The implantable stimulator may have a housing of a bio-compatible material. By "bio-compatible" is meant that the material from which the housing is made is unlikely to cause irritation when implanted in a patient's body and is unlikely to be rejected by an immune system of the patient's body.

Preferably, the housing is made of a plastics material, more particularly, a polymer material. The housing may define at least one suture opening for suturing the housing in position. Preferably, the housing defines a plurality of suturing openings extending for securing the housing to a predetermined location in the patient's body. It is intended that, in use, the stimulator will be implanted in a position in the patient's body where unimpeded movement, such as twisting, of the patient's body is still possible. A preferred location for the implantation of the stimulator is in a costal region of the body. Another region which could be considered is below an iliac crest of the patient's body.

The stimulator may be implanted, in use, in a substantially central location in the patient's body, the stimulator being connected to the sites in the patient's body to be stimulated via the electrodes and their associated leads to deliver the appropriate stimulation to the desired sites by dedicated, application-specific electrodes. It will be appreciated that, for this purpose, the leads of one group may differ in length from the leads of the other groups, the length of the leads of each group being governed by the site which is to be stimulated by that site.

It will be appreciated further that each patient's stimulation characteristics will differ from other patients so that the stimuli for that patient are unique to that patient. This will entail, for example, tailoring of stimulation pulses, as to amplitude, duration and frequency, so that the patient's sites are appropriately stimulated. Tailoring or calibrating the stimulator may be effected via the controller under the action of a clinician, as will be described in greater detail below. Data relating to stimulation characteristics for the patient and contained within the controller may be downloaded, via the interface unit, to a central storage site, such as, for example, a host computer or other non-volatile storage device.

The electrodes may be configured to be implanted in the patient's body by a surgical, subcutaneous tunnelling technique to reduce the number and size of the incisions to be made to the patient's body. Thus, due to the fact that each group of electrodes comprises separate leads, subcutaneous location of the electrodes is facilitated.

The receiving device of the stimulator may be in the form of an antenna. The device is, preferably, RF operable and, consequently, the antenna may be in the form of an RF receiver coil.

The transmitter may, in turn, be in the form of an RF transmitter coil arranged, in use, externally of the patient's body in register with the receiver coil so that RF signals are transmitted transcutaneously to the stimulator, in use.

The transmitter coil may be removably arranged with respect to the stimulator. The stimulator may include a retaining means for removably retaining the transmitter coil in position relative to the stimulator. The retaining means may be in the form of a magnet which cooperates with a complementary magnet carried by the transmitter coil so that the transmitter coil is held in position relative to the stimulator by magnetic attraction.

The controller may communicate with the transmitter via an implant interface of the communications interface unit using a dedicated, RF transmission protocol. The protocol may also incorporate reception telemetry for receiving data from the stimulator.

Preferably, the controller is in the form of a hand-held programmable device. Conveniently, the hand-held device may be in the form of a commercially available off the shelf unit while and the communications interface unit may be a custom designed, dedicated communications interface unit. For example, the programmable device may be in the form of a commercially available, pocket PC or PDA. To facilitate operation of the device, the PDA may have a display. The display may be a liquid crystal display (LCD) which may be used by the patient for providing operating instructions to the stimulator. Further, the LCD may be used by the clinician for programming the device to incorporate the unique stimulation characteristics for that particular patient. The programming feature of the controller may be password protected so that a patient is unable to alter or interfere with the program contained in the controller. Accordingly, the controller may be patient operable but clinician programmable.

The controller may include a memory card slot such as a compact flash (CF) memory card slot. Accordingly, the interface unit may include a CF interface card which interfaces to the PDA via a Compact Flash bus.

As indicated above, the interface unit includes an implant interface which interfaces with the stimulator. Still further, the interface unit may include a PC interface for enabling the PDA to communicate with a central database such as the host computer.

In addition, the interface unit may include a peripherals interface for enabling the controller to communicate with peripheral devices.

The peripherals interface may include a microphone interface for enabling the patient to issue voice commands to the controller via a microphone connected to the microphone interface.

Still further, the system may include a remote control facility which enables the patient to interact with the controller and, in turn, the stimulator remotely via one or more remote control units without the need for physically operating the controller. Preferably, each remote control unit provides the patient with a non-visual confirmation of communication of data from the remote control unit to the controller.

Thus, the peripherals interface may include a remote control interface. This may be a bi-directional communications interface between the remote control unit(s) and the controller. Also, this communications interface may be a wireless interface so as to minimise the necessity for fitment of cables and removing the possibility of cables becoming entangled or dislodged.

The interface unit may include an Input/Output (I/O) interface unit. This may be a software controllable I/O port. The port may be electrically isolated either on the interface unit itself or by use of in line isolation.

As indicated above, the system may include peripheral devices. One of the peripheral devices may be the remote control unit as described above. Other peripheral devices associated with the system may include sensor packs.

The peripherals interface may include a sensor pack peripherals interface for effecting communication with sensor packs, each sensor pack being provided to sense orientation of the patient's torso and extremities when exercising of the patient's extremities is to be performed or when the patient wishes to execute a standing, stepping or sitting operation. It will be appreciated that the orientation of the patient's extremities relative to the patient's torso is critical in carrying out these operations. Thus, the controller may receive data regarding the positioning of the patient's extremities via the sensor packs and the sensor pack peripherals interface.

The system may further include an external skin surface stimulating device which effects external stimulation, as opposed to subcutaneous stimulation, of certain of the patient's muscles.

BRIEF DESCRIPTION OF THE DRAWINGS

The invention is now described by way of example with reference to the accompanying diagrammatic drawings in which.

DETAILED DESCRIPTION OF THE INVENTION

Figures 20A, 20B:
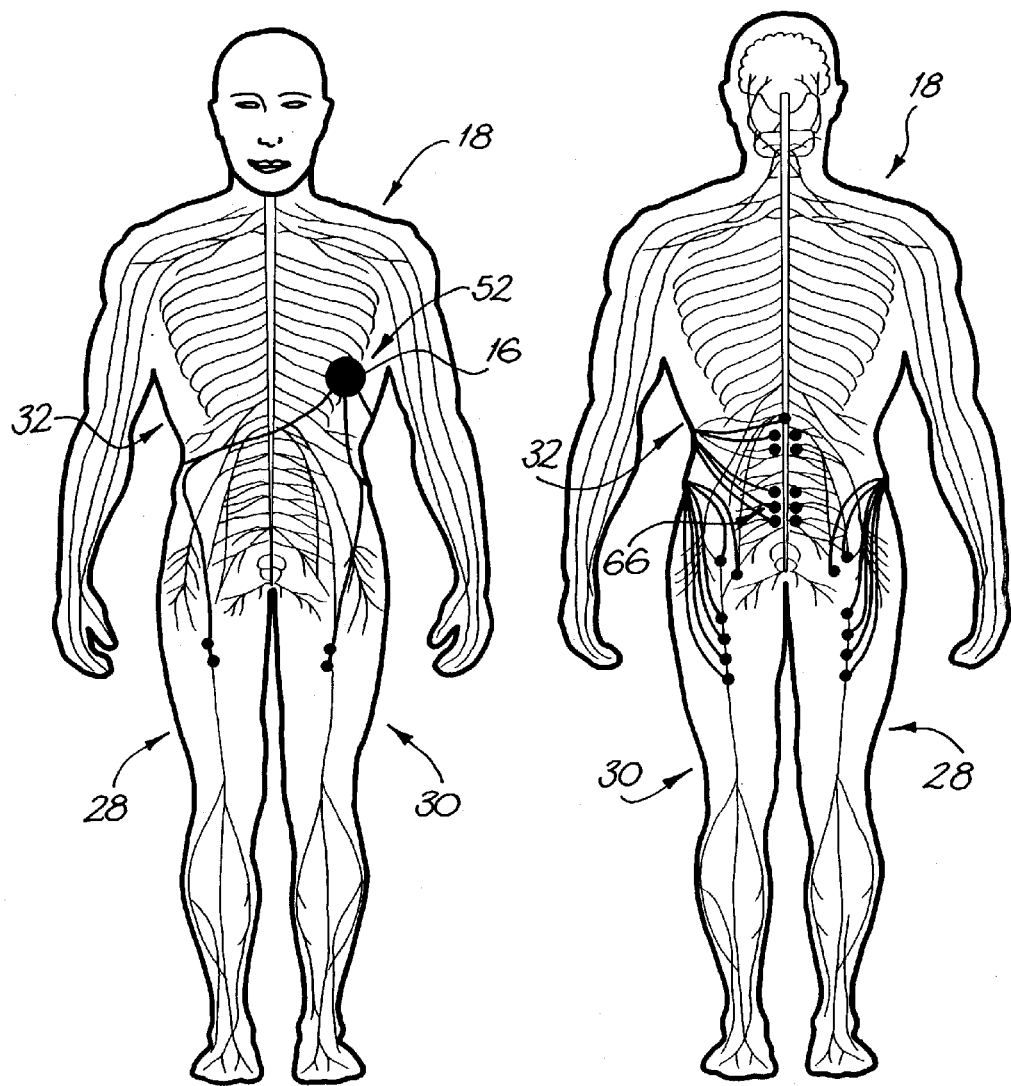
FIGS. 20a and 20b show a schematic representation of the implantable components of the system, in use.

In the drawings, reference numeral 10 generally designates a multi-purpose (FES) system in accordance with the invention. The system 10 includes a patient-implantable part 12 and an external part 14, the external part 14, in use, being arranged externally of a patient's body 18 (FIGS. 20a and 20b). The patient-implantable part 12 includes an implantable stimulator 16 for stimulating different sites in the patient's body 18. A plurality of leads and electrodes 20 extend from the stimulator 16, as will be described in greater detail below, for attachment to the various sites in the patient's body 18 to effect stimulation of those sites.

The external part 14 of the system 10 includes a controller 22 which controls the stimulator 16 via an externally worn transmission device 24.

The external part 14 of the system 10 further includes a plurality of sensor packs 26 in communication with the controller 22. The sensor packs 26 are mounted, in use, on the right lower extremity 28, the left lower extremity 30 and the torso 32 of the patient's body 18 for sensing the relative positions of the lower extremities 28 and 30 and the torso 32. It is envisaged that in applications directed towards controlling movement of the upper body and the arms, sensor packs 26 could also be positioned on regions of the arms and upper regions of the body for sensing the relative position of these regions in relation to overall body movement.

Figure 14:
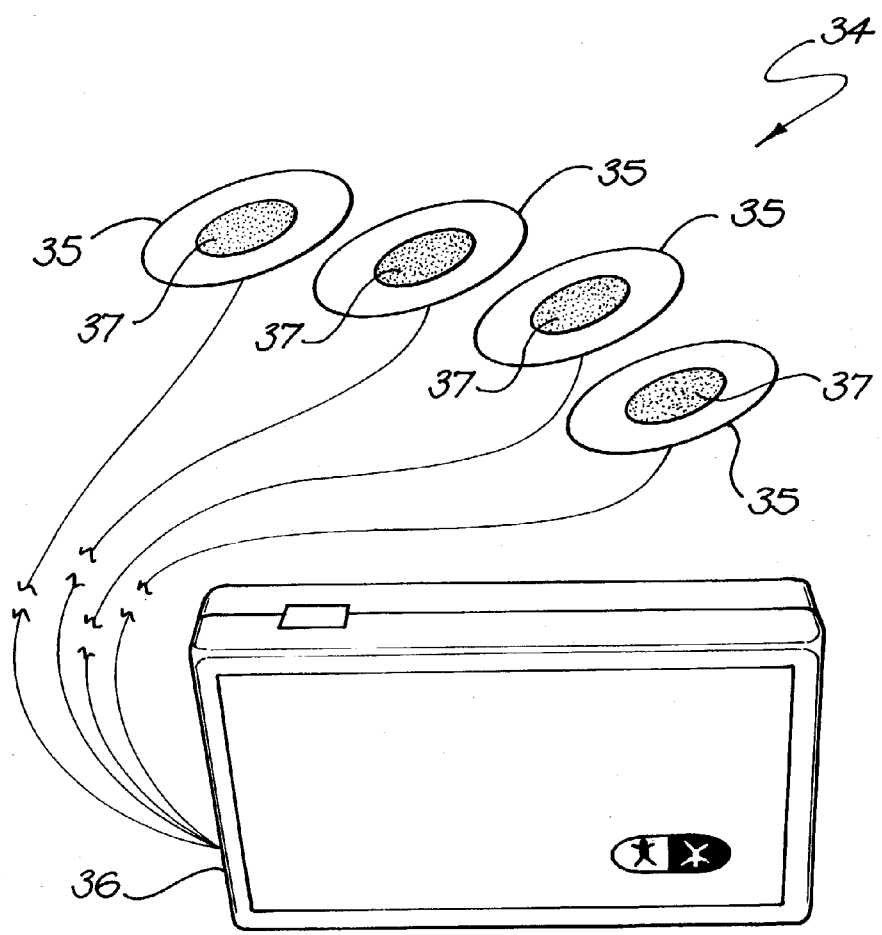
FIG. 14 shows a three dimensional view of an external stimulator unit for use with the system.

The controller 22 can also control an externally worn surface stimulator 34 instead of the implanted stimulator 16. A driver 36 of the external stimulator 34 is shown in FIG. 14 of the drawings. A plurality of pads 35 to be attached to the desired surface region of the patient's body 18 extend from, and are connected to, the driver 36 for externally stimulating predetermined sites of the patient's body 18. Each pad 35 can be adhesively attached to the skin surface by an appropriate adhesive region 37, thereby maintaining the pads firmly in place during use. The external stimulator 34 is usually used in place of the implanted stimulator 16 and not in conjunction with the implanted stimulator 16. For example the external stimulator 34 may be used to enable a person who is to undergo implantation of an internal stimulator 16 to commence training and to become accustomed to the effects achieved by neural stimulation. In any regard the controller 22 of the multi-purpose FES system 10 is capable of controlling the driver 36 of the externally worn surface stimulator 34 should such a stimulator be required by the system 10.

Figure 15:
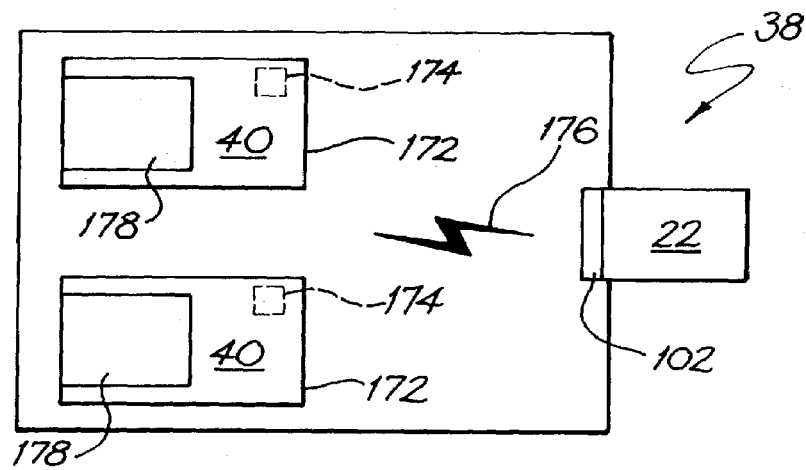
FIG. 15 shows a block diagram of an accessory for use with the system.

The external part 14 of the system 10 finally comprises a remote control system 38. The remote control system 38 comprises a plurality of remote control units 40 as shown in FIG. 15 of the drawings and discussed in more detail below.

Figure 3:
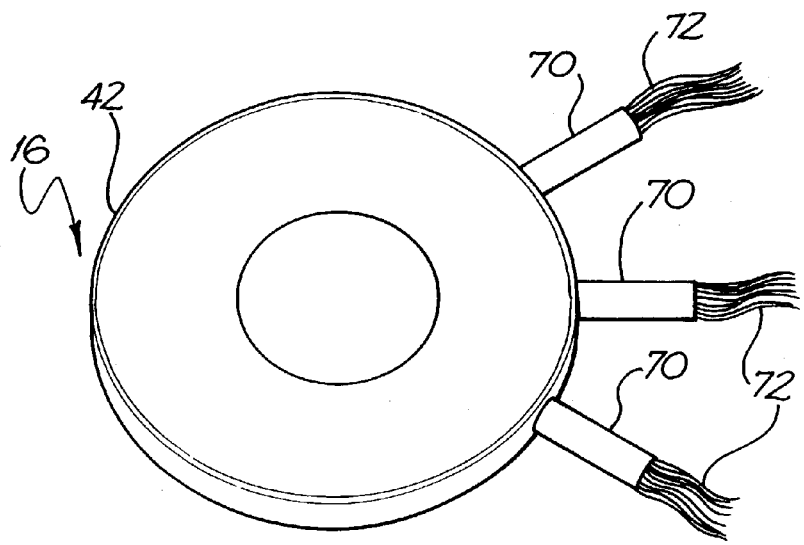
FIG. 3 shows a three dimensional view of an implantable stimulator for use with the system.
Figure 4:
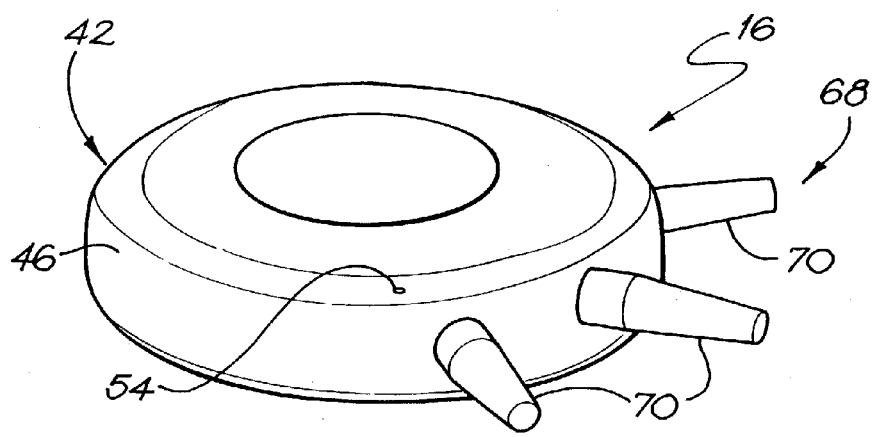
FIG. 4 shows a further, three dimensional view of the stimulator.
Figure 5:
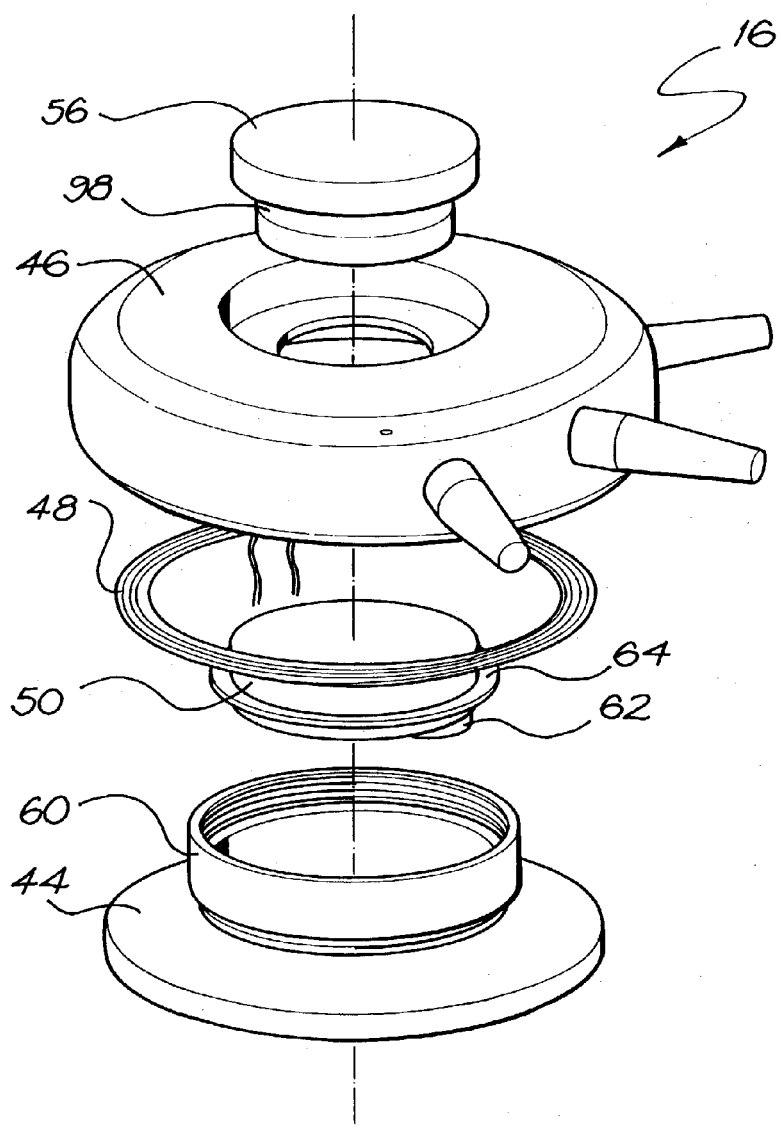
FIG. 5 shows an exploded view of the stimulator.

Referring now to FIGS. 3 to 5 of the drawings, the stimulator 16 is described in greater detail. The stimulator 16 comprises a housing 42 made up of a base 44 and a cover 46. The base 44 and cover 46 cooperate with each other to form an interior chamber or cavity in which a receiving device in the form of an RF coil 48 as well as a control unit or electronics package 50 are received.

In use, as shown in FIG. 20a of the drawings, the stimulator 16 is implanted in a costal region 52 of the patient's body 18. To secure the housing 42 of the stimulator 16 in position in the patient's body 18, a plurality of circumferentially spaced suture openings 54, one of which is shown in FIG. 4 of the drawings, extend through the housing 42 through each of which a suture is received.

The housing 42 is of a biocompatible material. Conveniently, the housing 42 is of a polymer material.

A first electrode 56 is carried on the cover 46. The base 44 of the housing 42 is of a metal material and forms a second electrode. The second electrode, formed by the base 44, and the first electrode 56 are, conveniently, titanium electrodes and, when the control unit or electronics package 50 is operating in a monopolar mode, the electrodes 44 and 56 act as a current return path.

Figure 1:
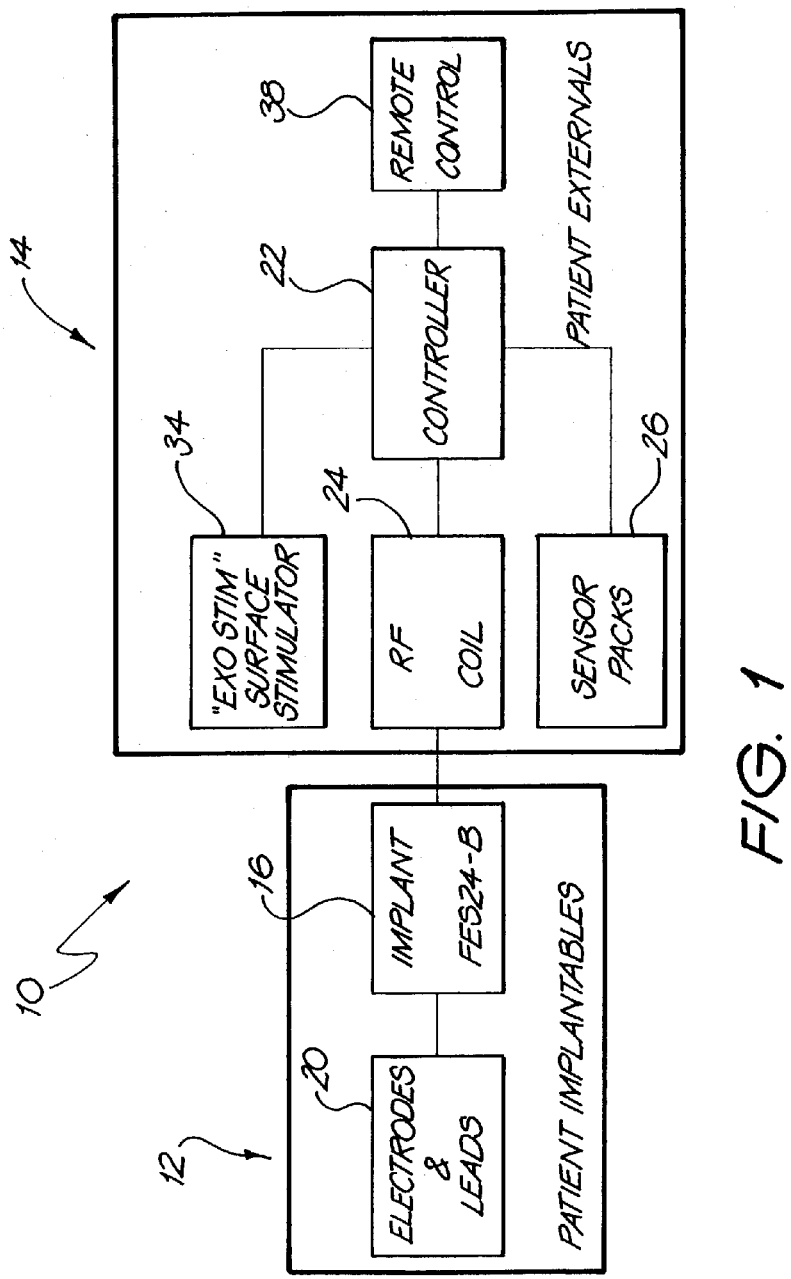
FIG. 1 shows a schematic, block diagram of a multi-purpose functional electrical stimulation (FES) system, in accordance with the invention.
Figure 2:
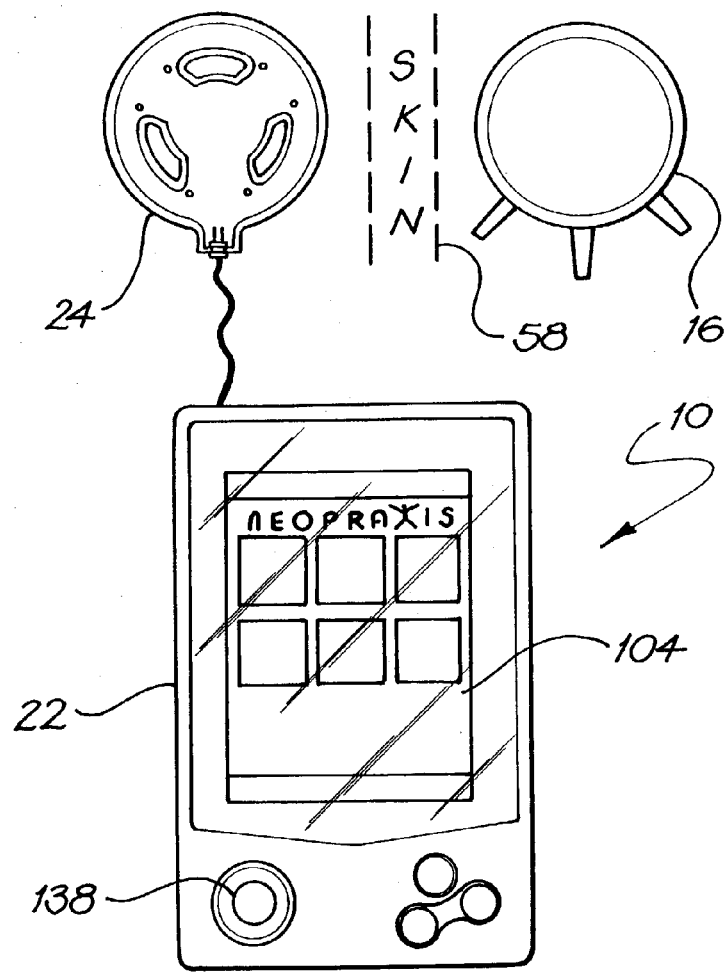
FIG. 2 shows a schematic representation of the system.

The RF coil 48 acts as a receiving antenna for receiving power and control signals from the controller 22 transcutaneously through skin 58 (FIG. 2) of the patient's body 18. The coil 48 consists of two two-turn coils connected in parallel, one inter-wound with the other. The coil 48 is made by winding two turns of platinum wire. The coil 58 is electrically isolated from the electrode system and plays no active part in stimulation.

Due to the inter-wound winding of the coils, the coil in fact is one turn thick and occupies a plane spaced from a plane of the electronics package 50 so as to inhibit feedback between the coil 48 and the electronics package 50.

The coil 48 further functions as a transmitting antenna which transmits data, via the transmission device 24, to the controller 22, the data relating to diagnostics of the stimulator 16. In addition, electrode potential measurements and physiological electrical activity is monitored by the electronics package 50 and data relating thereto are transmitted via the coil 48 and transmission device 24 to the controller 22. Hence, the stimulator is capable of measurements of some internal voltages, electrode stimulus voltages and samples of physiological potentials. Physiological potentials are measured voltages between active and reference electrodes. The reference electrodes are, normally, the electrodes 44 and 56.

The electronics package 50 is secured in position in the casing or housing 42 by means of a locating nut 60.

The electronics package 50 comprises pulse generating circuitry and in the embodiment shown is a passive device in the sense of having no internal power supply, the power being provided to the electronics package 50 via the coil 48. It is envisaged that the electronics package could also be provided with an internal power supply in the form of a rechargeable power source, such as a rechargeable battery.

The electronics package 50 consists of a printed circuit board (PCB) on which is mounted the appropriate circuitry for processing received signals from the controller 22. The PCB is mounted within a hermetically sealed titanium case 64 having a feed through device 62 to which electrical leads are connected.

The electronic components such as the electronics package 50 are hermetically sealed in an inert gas environment within the housing 42 of the stimulator 16. Such a seal inhibits the ingress of body fluids into the electronics package 50 thus inhibiting potential malfunctions. The seal also inhibits the migration of non-bio-compatible ions into the patient's body 18.

The electronics package 50 rectifies and decodes data received from the transmission device 24 to obtain power and receive data respectively. The electronics package, as indicated above, also provides the stimulation current to the electrodes under the control of the controller 22. Finally, the electronics package 50 measures, using telemetry methods, internal voltages and physiological potentials by means of the RF link.

The stimulator 16 operates using a 5 MHz carrier frequency. The radio frequency link utilises an embedded protocol and facilitates a stimulation rate of up to 14,400 pulses per second.

As described above, the system 10 is intended for multi-purpose stimulation of the patient's body 18. In particular, the system 10 is intended for stimulation of the posterior and anterior right lower extremity 28, the posterior and anterior left lower extremity 30, a posterior, sacral region 66 of the patient's spinal cord and at the conus of the patient's spinal cord. In this way, stimulation of at least four sites of the patient's body 18 can be effected.

For this purpose, the electrodes are arranged in separate bundles, one intended for each site of the patient's body.

Accordingly, the housing 42 of the stimulator 16 has three outlet ports 68, each of which terminates in a tube 70.

A bundle of leads 72 exits each tube 70 as shown more clearly in FIG. 3 of the drawings.

Each lead of the bundle 72 is constituted by a multi-strand conductor surrounded by a sleeve of an insulating material such as silicone. With this arrangement implantation of the leads of each bundle 72 is facilitated due to the fact that the leads of each bundle 72 can be spread through the patient's body in a distributed, flat manner rather than in the form of one, bulky cable. Thus, each bundle 72 of leads provides for convenient subcutaneous tunnelling to the lower extremities 28, 30 and the posterior, sacral region 66 of the patient's body 18.

Figure 17A:
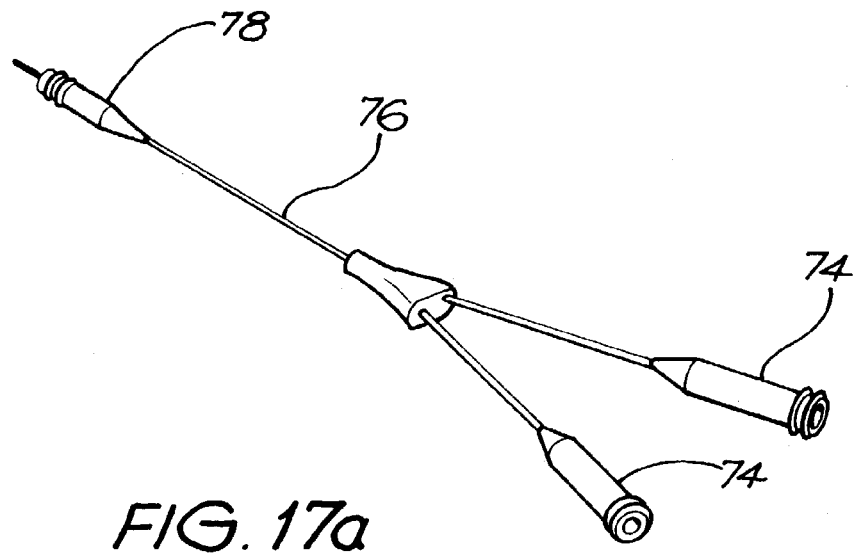
FIG. 17a shows a three dimensional view of a first type of lead used with the stimulator of FIG. 3.
Figure 17B:
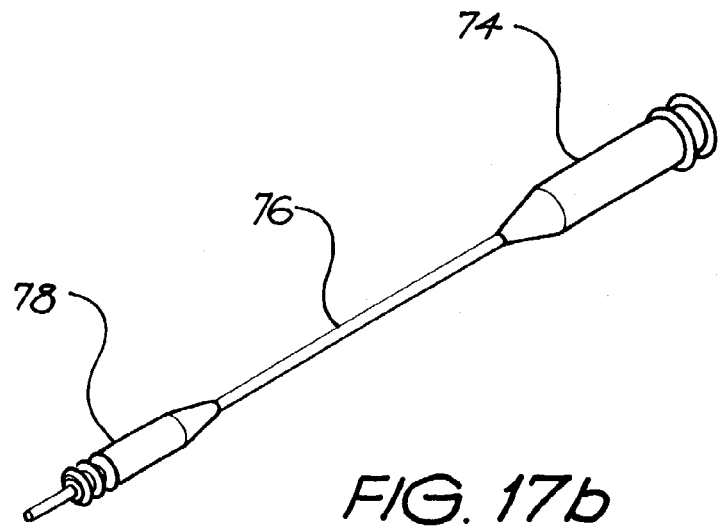
FIG. 17b shows a three dimensional view of a second type of lead used with the stimulator of FIG. 3.

Each lead of each bundle 72 terminates in a connector of the type shown at 74 in FIGS. 17a and 17b of the drawings.

Referring to FIGS. 17a and 17b of the drawings two versions of extension leads 76 are shown. The extension lead 76 of the type shown in FIG. 17a of the drawings has a male connector 78 at a first end. The lead 76 is bifurcated terminating in two of the connectors 74. The lead 76 shown in FIG. 17b of the drawings has a male connector 78 at a first end and terminates in a female connector or socket 74.

In use, one bundle 72 of either 8 or 9 leads intended for the right lower extremity 28, one bundle of either 8 or 9 leads intended for the left lower extremity 30 and one bundle of either 6 or 4 leads intended for the posterior, sacral region 66 of the patient's spinal cord extend from the housing 42 of the stimulator 16. These two bundle configurations are known as "9+9+4" or "8+8+6".

A suitable electrode may be connected to each lead in each bundle via the connector in which that lead terminates. It will be appreciated that each connector or socket carries an appropriate identifying label.

The electrode in question may be connected to its associated lead either directly or via one of the extension leads 76.

Figure 18:
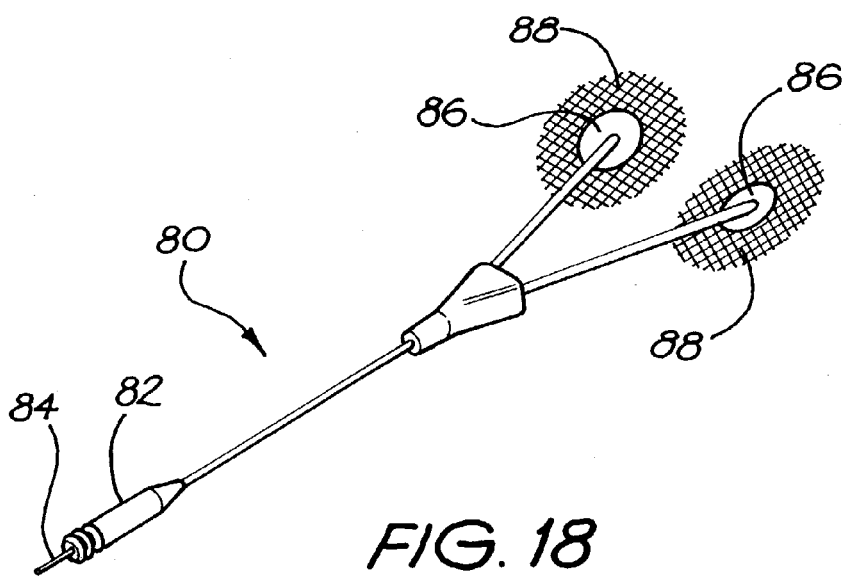
FIG. 18 shows a three dimensional view of a first type of electrode for use with the system.

For the right lower extremity 28 and the left lower extremity 30, a plurality of electrodes 80 of the type shown in FIG. 18 of the drawings is used. The electrode 80 comprises an insulated conductor 82 terminating, at one end, in a connector 84 which engages the socket of its associated lead or extension lead 76, as the case may be. An opposed end of the insulted conductor 82 is bifurcated and each bifurcation terminates in a button-type electrode element 86.

Each electrode element 86 is surrounded by a backing member which in use is sutured to tissue surrounding the nerve to be stimulated. The backing member is made of a biocompatible material such as a suitably reinforced silicone material. Each electrode element 86 is of a platinum material which is placed in abutment with the nerve to be stimulated in the right lower extremity 28 or left lower extremity 30, as the case may be.

Figure 19:
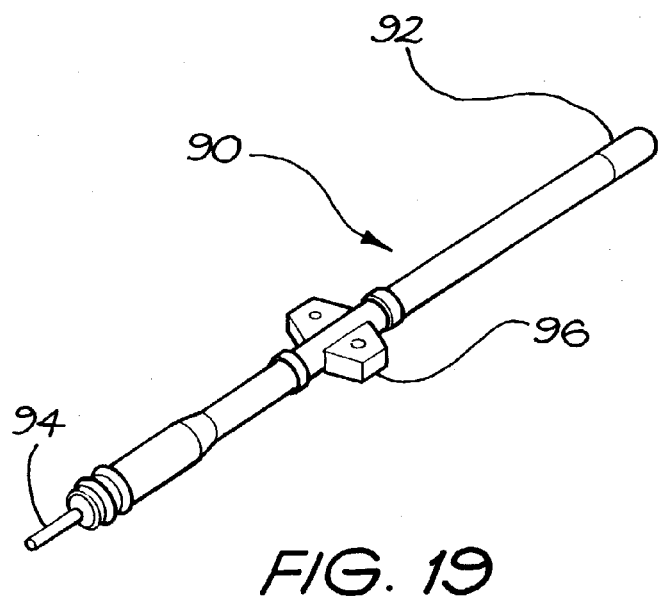
FIG. 19 shows a three dimensional view of a second type of electrode for use with the system.

To stimulate the posterior, sacral region 66 of the patient's spinal cord use is made of a plurality of electrodes 90 of the type shown in FIG. 19 of the drawings. This electrode 90 has a platinum electrode tip 92 at its distil end with a connector 94 at its proximal end. Once again, each electrode 90 is connected either directly to one of the leads of the relevant bundle 72 or via one of the connectors 76.

The electrodes 90 are used to stimulate the sacral roots of the spinal cord for bladder, bowel and erection control. The electrodes 90 are, in use, inserted through the sacral foramina so that they lie adjacent the appropriate sacral roots. The applicant believes that this method of insertion obviates the need for surgical procedures such as laminectomies which, as far as the applicant is aware, were previously required for FES bladder control.

Each electrode 90 is supplied with a stiffening stylet 96 and an insertion tool to aid in placement.

It will be appreciated that, in use, the transmission device 24 needs to be placed in register with the implanted stimulator 16 so that transcutaneous communication can take place between the stimulator 16 and the transmission device 24. To facilitate retention of the transmission device 24 in position relative to the stimulator 16, the stimulator 16 includes a retaining means in the form of a permanent magnet 98. The magnet 98 is removably mounted in the cover 46 of the housing 42 of the stimulator 16. The magnet 98 is retained in position by the first electrode 56 which is removably mounted with respect to the housing 46.

The magnet 98 is a rare earth, permanent magnet which is hermetically sealed in a titanium case. The titanium case is defined by the electrode 56 and has a marking on it to indicate the polarity of the magnet 98. Because the electrode 56 is removably mounted with respect to the housing 42 of the stimulator 16, the magnet 98 is able to be surgically removed without removing the entire stimulator 16 or damaging the stimulator 16. Hence, in use, an incision would be made in the skin 58 of the patient to enable the magnet 98 to be removed. It will be appreciated that removal of the magnet 98 is required if the patient, for example, is required to undergo magnetic resonance imaging (MRI) investigations.

The stimulator 16 displays radio-opaque identification markings (not shown) for non-invasive post-operative identification. These markings could include details such as the manufacture's name, model number, year of manufacture, or the like.

Figure 6:
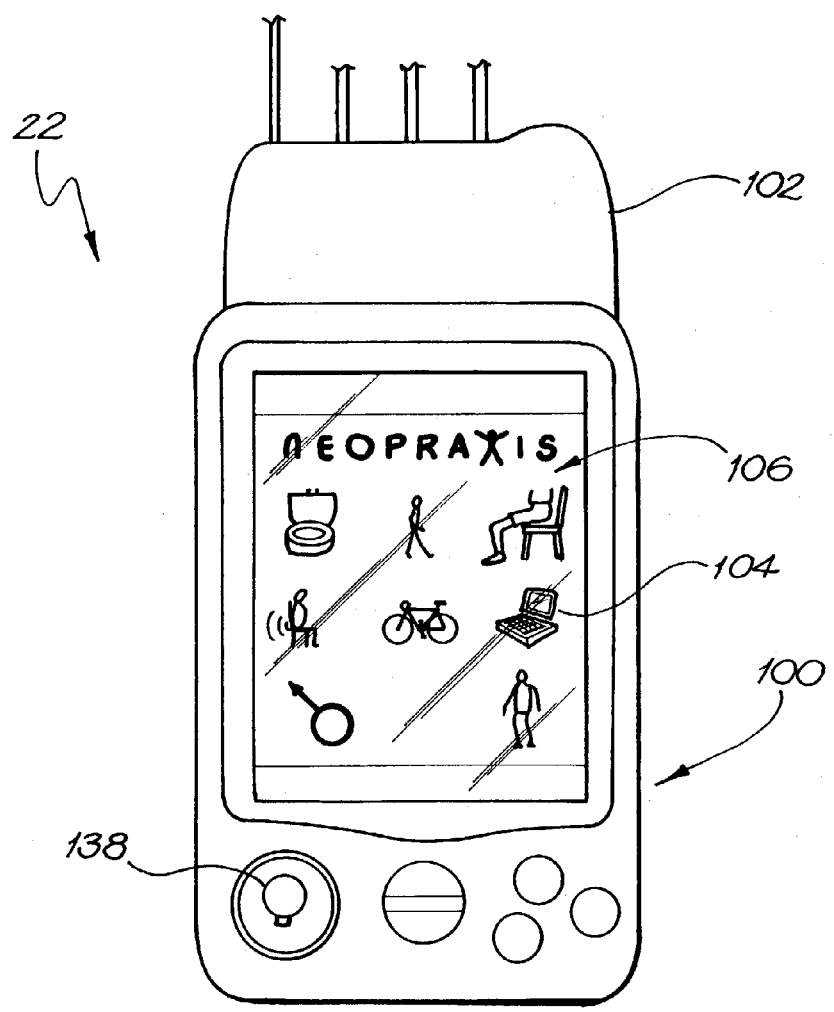
FIG. 6 shows a front view of a controller for use with the system.
Figure 7:
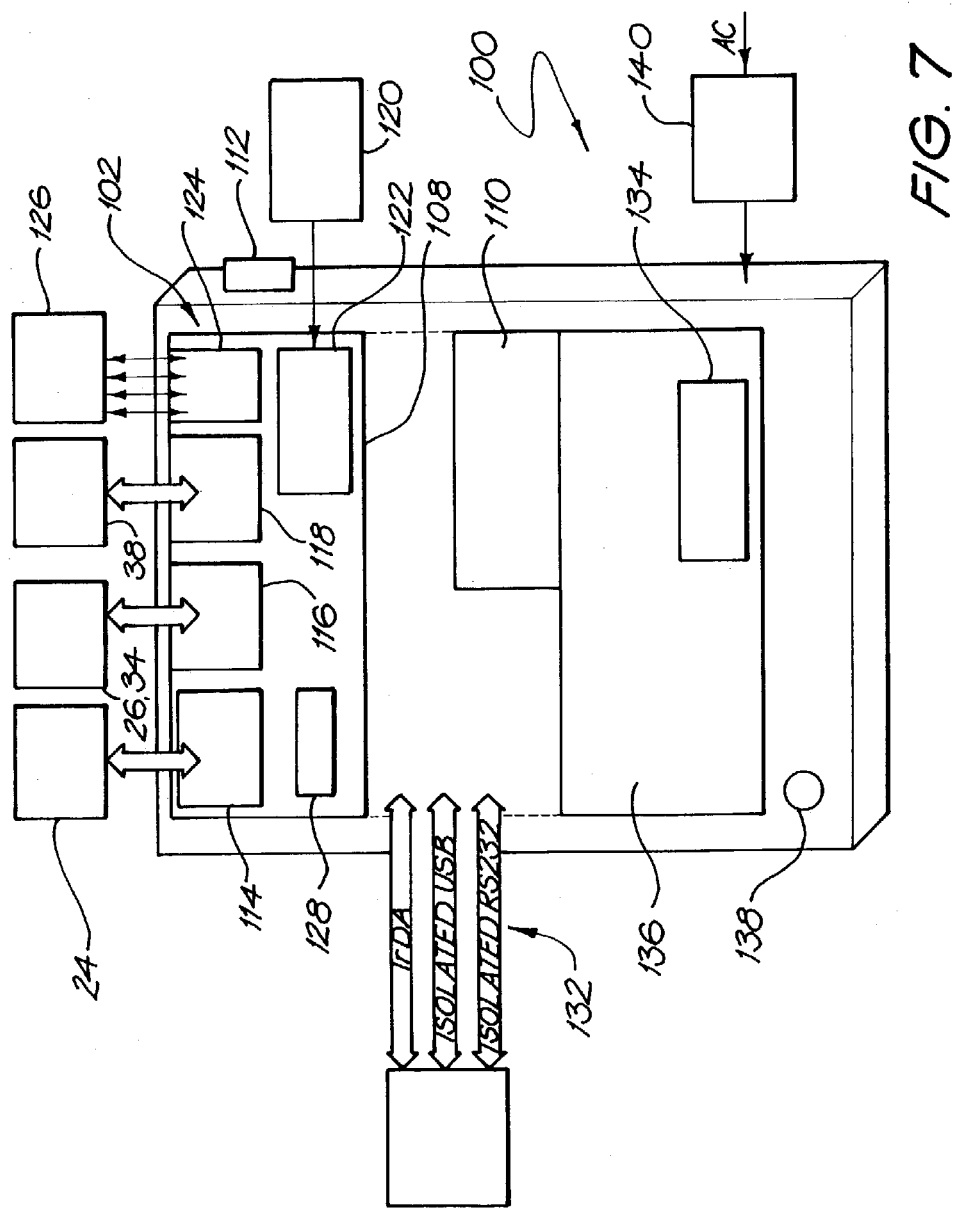
FIG. 7 shows a block diagram of the controller.

Referring now to FIGS. 6 to 8 of the drawings, the controller 22 is described in greater detail.

The controller 22 is worn externally of the patient's body 18. The controller 22 includes a patient-operable, clinician-programmable control device 100. The control device 100 is in the form of a hand-held programmable device. Preferably, the control device 100 is in the form of a commercially available, pocket PC or PDA. The control device 100 communicates with components of the external part 14 of the system 10 and the stimulator 16 via a controller interface 102. The controller interface 102 interfaces to the control device 100 via a compact flash port of the control device 100. The controller interface 102 facilitates bi-directional communication between the stimulator 16 using the transmission device 24.

Figures 8A, 8B:
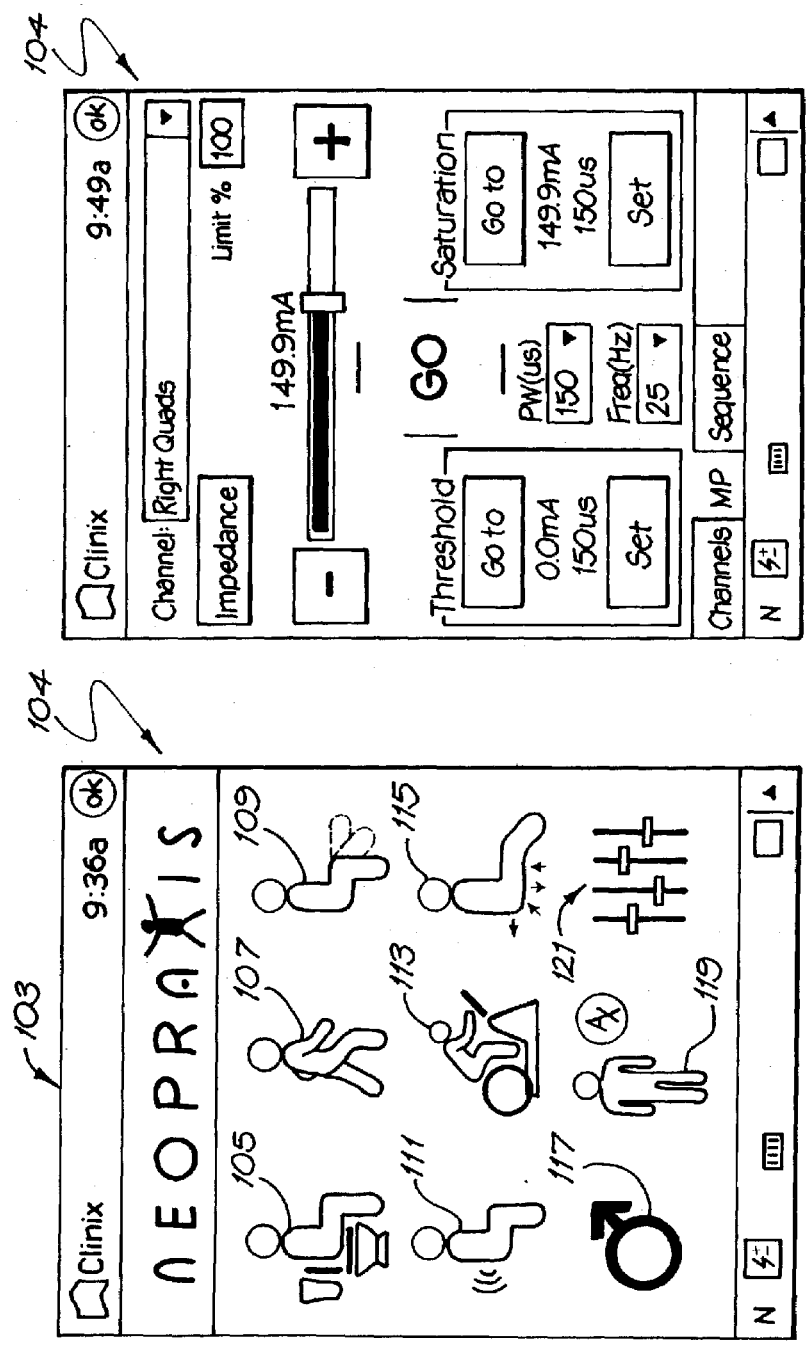
FIGS. 8a–8c show screen displays of the controller.
Figure 8C:
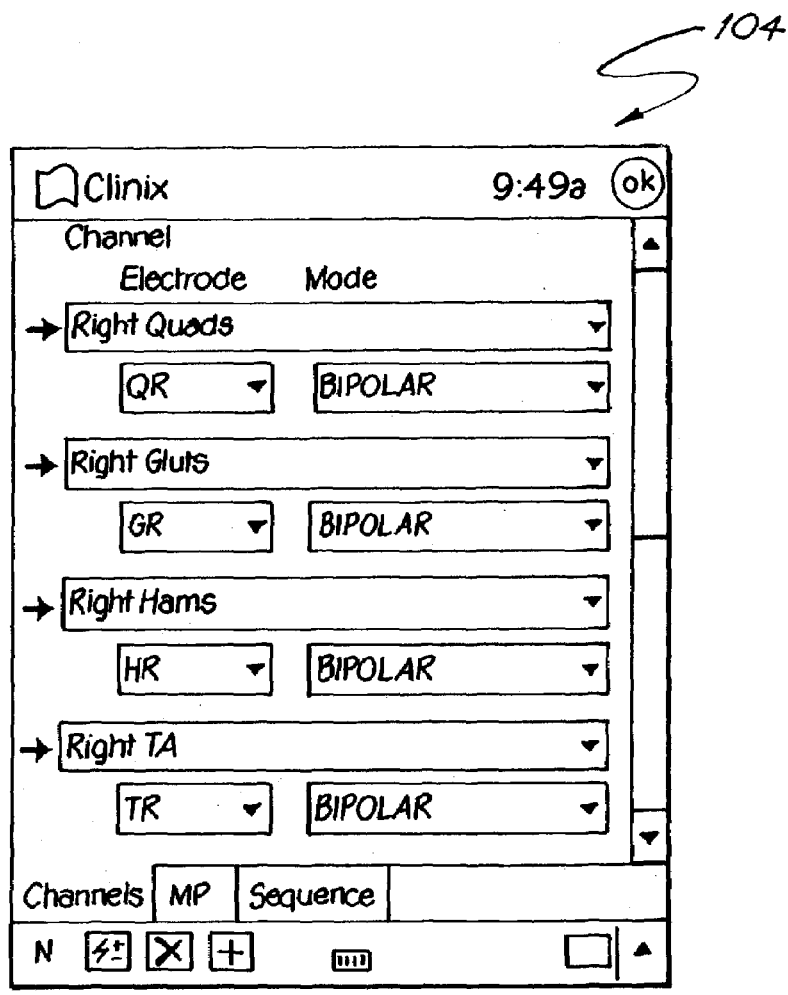

The control device 100 includes a display in the form of a liquid crystal display (LCD) 104. Preferably, the LCD 104 is implemented in the form of a touch-sensitive screen for enabling the patient to select, via appropriate icons 106 on the screen, the stimulation to be effected. Further, as shown in FIGS. 8a–8c of the drawings the screen display can be changed, particularly as shown in 8b and 8c of the drawings, to enable a clinician to program the device, as will be described in greater detail below.

The controller interface 102 includes a card 108 (FIG. 7) which enables the control device 100 to interface with various peripheral devices. The device 100 includes a card driver 110. The card 108 is a CF+card with the driver 110 being a CF+card driver. A card lock 112 is provided on a side of the control device 100 for locking the card 108 in position.

The interface card 108 firstly includes a stimulator interface 114 for interfacing with the implanted stimulator 16 via the transmission device 24. Secondly, the interface card 108 includes a peripherals interface 116 in the form of a queried serial port interface (QSPI) for interfacing with the sensor packs 26 and the external stimulator 34. A remote control interface 118 is included for communicating with the remote control system 38 of the system 10.

The controller 22 makes use of an external microphone 120. The external microphone 120 is worn close to the patient's mouth for enabling the patient to issue oral commands to the controller 22. Accordingly, the interface card 108 includes a microphone interface 122 for communicating with the microphone 120.

Finally, the interface card 108 includes an I/O interface 124 which may be software controllable for various optional uses as indicated by reference numeral 126.

Each system 10 is dedicated to a particular patient. Accordingly, the interface card 108 may include a unique serial number 128 which is read by the control device to ensure that it is compatible with the software of the control device 100.

The control device 100 is able to communicate with a host station such as a personal computer (PC) 130 via a data bus 132. In this way, data from the control device can be downloaded to the PC 130 or uploaded from the PC 130. The control device 100 is able to operate with a non-volatile CF memory card via the data bus 132. In this way, data from the control device can be downloaded to a CF memory card or uploaded from a CF memory card.

As indicated above, the control device 100 is programmable by a clinician for a particular patient. It will be appreciated that each patient's stimulation characteristics are different and that stimulating pulses for each patient need to be tailored for that particular patient. Thus, pulses of predetermined duration, amplitude and frequency need to be determined for each particular patient. The tailoring of the stimulator 16 may be effected by the control device 100 under the action of the clinician. This data, amongst other data, may be downloaded to the PC 130 via the data bus 132.

The tailoring characteristics of the patient are stored in a database 134 in the control device 100.

Applications software 136 is also stored in the control device 100. The applications software is referred to by the applicant as its "Clinix" software and is run under the operating system of the control device 100. For example, the operating system may be Microsoft's Windows CE operating system (Microsoft, Windows and Windows CE are registered trade marks of Microsoft Corporation). The applications software 136 is written in C++ computer language. The software 136 provides an environment for programs which control stimulation in order to produce a desired outcome. These programs are referred to by the applicant as "Strategies". Thus, the software provides an environment for Strategies for, for example, neuromodulation, sit-stand-sit, stepping, exercise, bladder control and seated pressure relief in which to operate. The software's operation is configurable via built in programming system functionality in the applications software 136. The software 136 is also designed so as to minimise the risk of unintentional stimulation. Finally, the software 136 is configured so as to be inoperable unless the interface card 108 is inserted in the control device 100 and is locked in position via the card lock 112.

As mentioned above, the Strategies are selected from a screen of the control device 100 by selecting the appropriate icon. FIG. 8a shows a screen display 103 of the Strategies capable of being selected by the patient. The patient can select from bowel/bladder Strategies (icon 105), upright mobility Strategies (icon 107), lower limb exercise Strategies (icon 109), neuromodulation Strategies (icon 111), bicycle exercise Strategies (icon 113), pressure relief Strategies (icon 115) and impotence control Strategies (icon 117). As shown there are also icons (icons 119 and 121) available for access by a clinician to obtain a patient assessment as well as to access a motorphysics/patient programming facility.

A number of these Strategies are now described in greater detail below.

The Strategy represented by the first icon 105 is a "bladder" Strategy which provides the patient with the ability to initiate activation of the detrusor or sphincter muscles for the purposes of bladder control. An "empty bladder" Strategy is provided where the electrodes 90 stimulate the patient's anterior sacral roots to achieve bladder control. In this regard, it is to be noted that the detrusor muscle is a smooth slow acting muscle while the sphincter is a fast acting skeletal muscle. The nerves which innervate the detrusor and sphincter muscles are stimulated by a pulsating set of stimulations, eg 15 Hz for 3 to 4 seconds with 10 seconds inter-stimulus gap, using the electrodes 90 in the posterior, sacral region 66 of the patient's spinal cord. During off periods, the sphincter opens quickly while the detrusor continues to compress the bladder to provide pulsatile voiding.

The Strategy represented by the second icon 107 is an upright mobility Strategy which provides the patient with the ability to initiate movement of the body or maintain a stable body position. This Strategy includes a "stand" Strategy where the electrodes 80 are stimulated in a coordinated manner to implement a "stand" function. Closed loop control is provided using the sensor packs 26. A further Strategy is a "step" Strategy where, once again, the electrodes 80 are stimulated in a coordinated manner to implement a "step", but only after the "stand" Strategy has been completed. A closed loop control system is achieved using the sensor packs 26. While the patient is standing, a "sit" Strategy may be implemented where, once again, the electrodes 80 provide stimulation in a coordinated manner to implement a "sit" function using closed loop control provided by the sensor packs 26.

The strategy represented by the third icon 109 is a strategy for exercising the lower extremities 28, 30. Lower extremity exercise provides the patient with the ability to initiate movement of the lower extremities 28, 30 so as to increase muscle strength, decrease fatigue and increase muscle bulk. Muscles in the lower extremities 28, 30 are stimulated so as to produce an exercise effect such as, for example, knee extensions using the electrodes 80 implanted in the lower extremities 28, 30.

The next icon 111 represents a neuromodulation Strategy stimulating at the level of the conus and/or the sacral roots to keep the bladder a-reflexive. In contrast to current surgical techniques which require the cutting of some posterior, sacral root nerves (a sacral posterior rhizotomy) in order to prevent interference with the bladder control system by disordered reflex activity, neuromodulation techniques utilising high rate stimulation are employed in an attempt to obviate this surgical procedure.

The next icon 113 represents an exercise bicycle Strategy which can be employed by the patient when present on an exercise bicycle. In this routine the lower extremities 28, 30 can be stimulated in a controlled manner to effect a pedalling motion with feedback provided by strategically placement of the sensor packs 26 on the lower extremities 28, 30. The controller 22 monitors and controls the speed of the cycling motion by controlling the frequency and amplitude of the stimulation applied to the lower extremities 28, 30.

A further Strategy represented by the icon 115 is a "seated pressure relief" Strategy. This Strategy provides the patient with the ability to initiate activation of the gluteal muscles adequately to shift body weight and relieve seated pressure. Electrodes 80 of the type illustrated in FIG. 18 of the drawings are used to stimulate the gluteal and other muscles periodically to shift the patient's weight while sitting. A warning signal with delay is provided to the patient prior to initiating stimulation.

The next icon 117 represents a Strategy to control impotence and erectile dysfunction in male patients. By selecting this icon 117 the patient can control erectile function ensuring that the appropriate stimulation is applied in the necessary manner to maintain an erection.

To enable tailoring of the system 10 for a particular patient's needs, the controller 22 is operable in a "Motorphysics" state which enables the clinician to collect strategy-independent parameters required for stimulation such as stimulation current level, frequency and pulse width. This facility is accessed by the clinician touching icon 121 on the screen 104 of the control device 100. Thus, the clinician can place the control device 100 in a Motorphysics state, as shown in FIGS. 8b and 8c of the drawings, for enabling the parameters to be set and to facilitate parameter measurements and system configuration capabilities. In this mode the clinician can also configure the controller 22 with patient-specific strategies and can customise the controller 22 with a particular set of operational parameters.

The stand, step and sit Strategies discussed above are mutually exclusive. However, in the Motorphysics mode, any one of those states are individually accessible by the clinician. Further, the "step" Strategy and the "sit" Strategy are only accessible once initiation of the "stand' Strategy has been completed. In addition, the upright mobility modes, being the "stand", "step" and "sit" Strategies are mutually exclusive with respect to the seated, pressure relief Strategy.

In general, the Clinix applications software 136 provides a means for the clinician to access clinician-only capabilities. Thus, the software 136 may be password protected and the password is changeable by a clinician upon entry of an existing password using the icon 119.

Operation of the controller 22 in the Motorphysics mode is a clinician-only capability. The applications software 136 also provides a means of determining which Strategies have been loaded into the control device 100 and allows the clinician to enable and disable functions. The applications software 136 also allows the clinician to select a Strategy to implement a function and to select modules for selected Strategies.

The control device 100 includes a "hibernate" switch 138. The applications software 136 inhibits operation of this switch 138 except when the main strategy selection menu is being shown.

The applications software 136 inhibits initiation of any Strategy if the battery power level of the control device is low and provides a regular low battery warning. In this regard, the control device 100 continues to operate continuously for at least one minute after a low battery warning has issued prior to shutting down.

The battery of the control device 100 provides for a minimum of 8 hours continuous operation. The battery may be a re-chargeable battery and the control device 100 includes a battery charger.

As indicated above, the controller 22 communicates with the implanted stimulator 16 via a transmission device 24. The transmission device 24 is shown in greater detail in FIGS. 10 to 13 of the drawings. Because the transmission device 24 is to be worn for extended periods by the patient, it needs to be of a resiliently flexible material to facilitate maximum comfort during use by the patient.

Thus, the transmission device 24 has a carrier 142 of a resiliently flexible silicone material. More particularly, the carrier 142 is a printed circuit board (PCB) also of a resiliently flexible material. An RF coil (not shown) is carried on a first side of the PCB 142. The RF coil is, conveniently, constituted by a turn etched on to the first side of the PCB 142.

An opposed side of the PCB 142 carries an LRC tuning circuit 144 of which the coil forms a part. The tuning circuit 144 renders the transmission device 24 tunable. The tuning circuit 144 includes a pair of fixed value capacitors 146 connected in parallel with a variable capacitor 148. Tuning of the circuit 144 is facilitated by the variable capacitor 148.

A connector plug 150 is carried on the same side of the PCB 142 as the tuning circuit 144.

The PCB 142 has a coating 154 of a bio-compatible, plastics material. The coating 154 encases the PCB 142.

In the manufacture of the transmission device 24, the PCB 142 is assembled and a magnet 152 is placed in position on the PCB 142 on the same side of the PCB 142 as the tuning circuit 142. Thereafter, a first part 156 of the coating 154 is applied to that side of the PCB having the coil. Tuning of the transmission device 24 is effected via the variable capacitor 148 where after the variable capacitor is sealed by application of the second part of the coating 154 so that the variable capacitor 148 cannot be accessed to inhibit adjustment or variation of the tuning by an unauthorised person.

The PCB 142 has a plurality of openings 158 defined through it. When the first part 156 of the coating 154 is applied to the PCB 142, the part 156 has portions 160 protruding through the openings 158 which adhere to the second part of the coating 154 when the second part of the coating is applied. Conveniently, the coating 154 is of a silicone material.

A cable from the interface 102 of the control device 100 is received in the connector 150 to establish the link between the transmission device 24 and the controller 22.

In use, the transmission device 24 is placed against the patient's skin 58 (as shown schematically in FIG. 2 of the drawings) in register with the implanted stimulator 16. The transmission device 24 is held in position relative to the stimulator by magnetic attraction between the magnet 152 of the transmission device 24 and the magnet 98 of the stimulator 16.

Figures 16A, 16B:
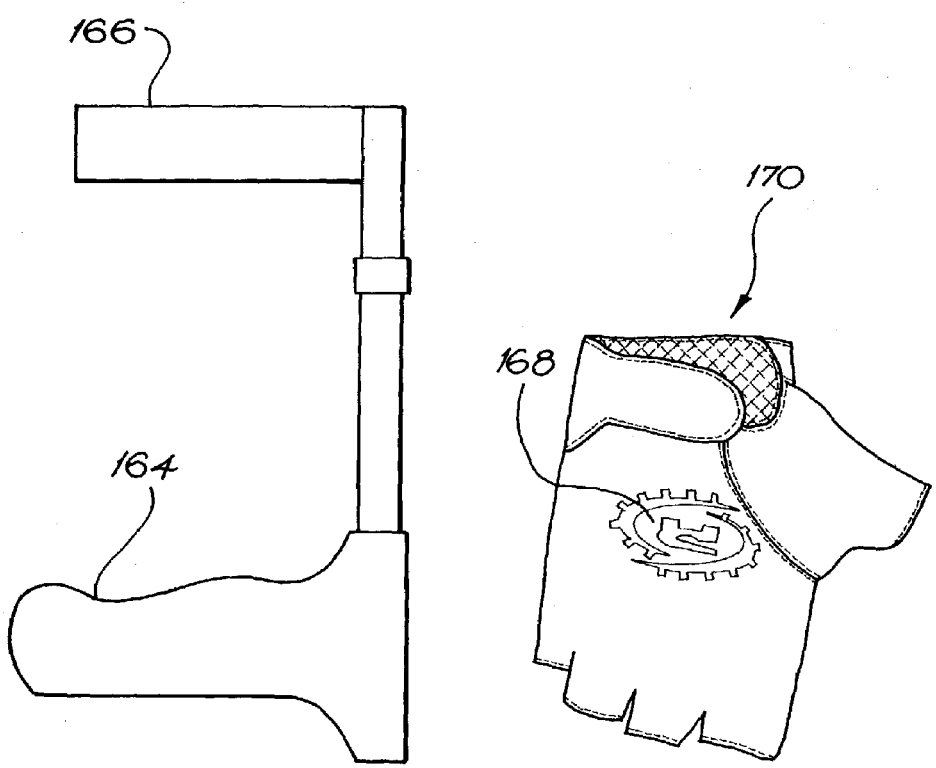
FIG. 16a shows a side view of part of a first item of equipment incorporating a component of the accessory of FIG. 15.
FIG. 16b shows a plan view of a second item of equipment incorporating a component of the accessory of FIG. 15.

The system 10 includes the remote control system 38 which enables a patient fully to control live mode operation of the system 10 without necessitating direct interaction with the controller 22. The controller 22 can then be mounted in a body worn pouch or on the belt of the user. The remote control system 38 comprises a plurality of remote control units 40 (FIG. 15). The remote control units 40 may be arranged in various items of equipment used by the patient. For example, as shown in FIG. 16*a* of the drawings, a remote control unit 40 could be mounted in a hand grip 164 of a crutch 166. An index finger operable remote control unit 40 could be mounted in a palm region 168 of a glove 170 as a shown in FIG. 16*b* of the drawings. Other items of equipment which may incorporate remote control units 40 include a beam of a parallel bar exercising apparatus, a walking frame, or the like.

Each remote control unit 40 includes a carrier 172 which is mounted on the item of equipment with which the remote control unit 40 is to be used. The carrier 172 carries various electronic components thereon including a transceiver unit 174. The transceiver unit 174 enables a bidirectional, wireless link 176 to be established between each remote control unit 40 and the controller interface 102 of the controller 22.

Further, each remote control unit 40 includes a non-visual annunciator which provides feedback to the patient alerting the patient to receipt of command carrying data by the controller 22. With the non-visual annunciator 178, the need for the patient to obtain visual feedback that the controller 22 has received a command is obviated. Preferably, the annunciator 178 is an audible annunciator or a tactile annunciator such as a vibratory device.

Each remote control unit 40 includes from 1 to 4 control switches which enables the patient to communicate a desired command to the controller 22, for example, while the patient's hands are otherwise occupied. The annunciator 178 ensures that the patient receives confirmation that the controller 22 has received the command without the need for the patient to have sight of the controller 22.

Only one of the remote control switches is able to be operated by the patient at any one time to ensure that only one command is received by the controller at any one time.

Further, even though the remote control system 38 may include a number of remote control units 40, only one remote control unit 40 may be able to be operated by the patient at any one time.

It will be appreciated that it is important that the system 10 only operates with the remote control units 40 of that particular system. Hence, each remote control unit 40 has a unique identity code associated with it which is recognised by the associated controller 22 of that system 10. Thus, any data transmitted by any remote control unit 40 of the remote control system 38 includes an identification key or code which is embedded in that data as it is transmitted so that the remote control unit 40 only activates its associated controller 22.

In addition, data transmitted by the transceiver unit 174 of any remote control unit 40 includes authentication data to inhibit spurious transmissions activating the controller 22.

The authentication data is in the form of a checksum which is transmitted with the data from the transceiver 174 of the remote control unit 22.

Each remote control unit 40 is able to be interrogated by its controller 22 to monitor the operational status of the remote control unit 40.

Each remote control unit 40 also has a measure of self-diagnostic ability in the sense that, being battery-operated, each remote control unit 40 can monitor its battery and alert the controller 22 when the battery becomes or is low. If it should be found that the operational status of any remote control unit 40 is inadequate, the navigator 22 can implement a strategy shut down in a safe manner and alert the patient simultaneously.

As described above, the system 10 enables the patient to implement various Strategies, in particular, upright mobility Strategies such as "stand", "step" and "sit". Sensor packs 26 are attached to the lower extremities 28, 30 and torso 32 of the patient's body 18 to monitor positional status of these parts of the patient's body 18 when the upright mobility Strategies and exercise Strategies are implemented. The sensor packs 26 provide closed loop control to facilitate safe stand-up, sit-down, standing and stepping functionality.

Figure 9:
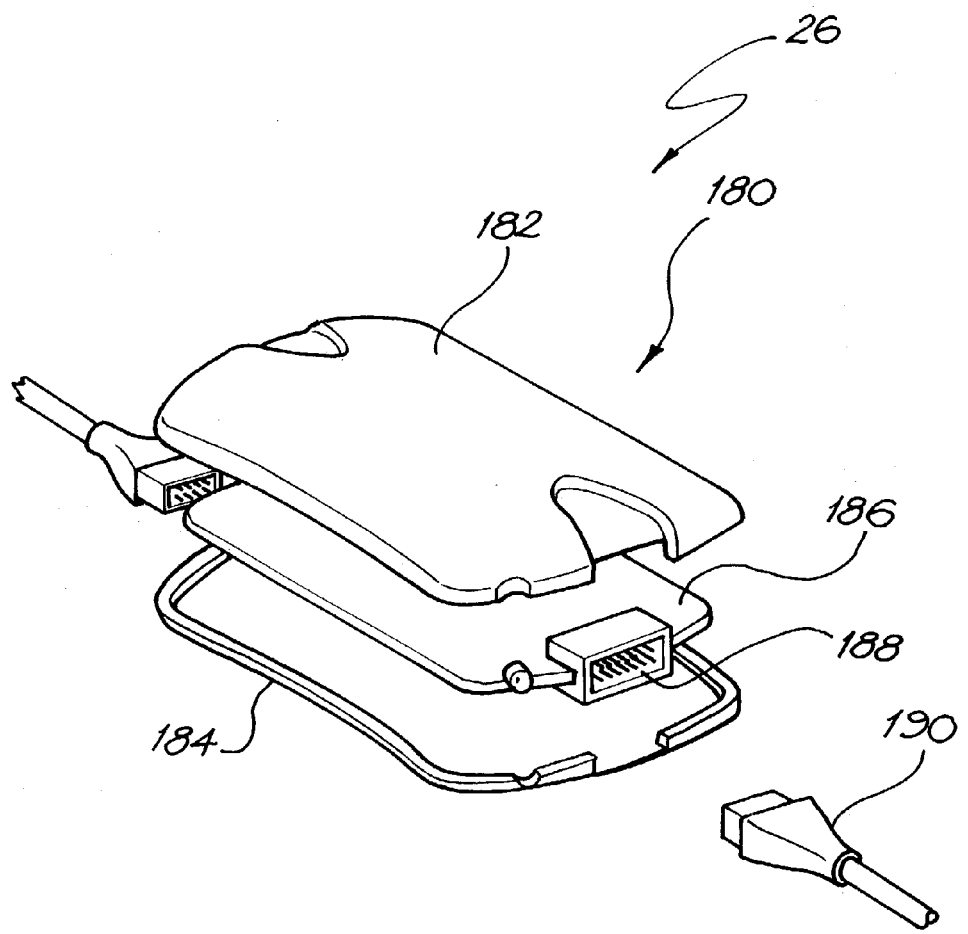
FIG. 9 shows a three dimensional, exploded view of a sensor pack for use with the system.
Figure 10:
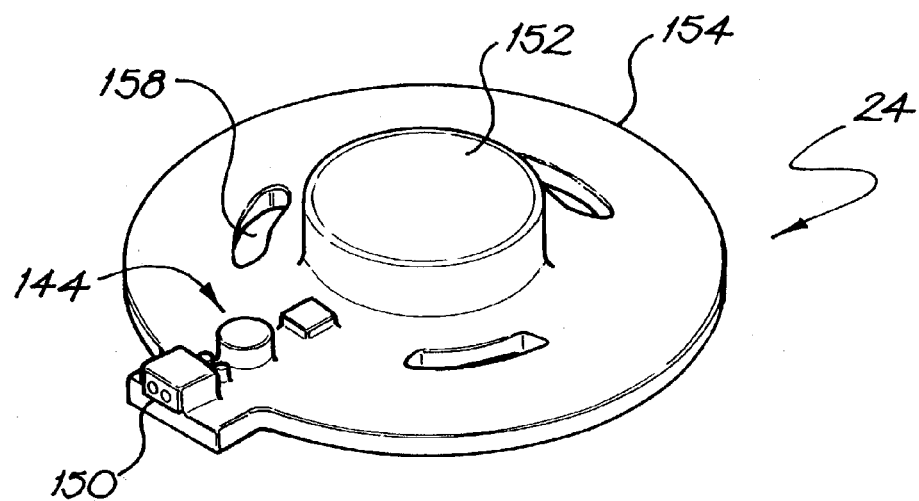
FIG. 10 shows a three dimensional view of a transmission device for use with the system.
Figure 11:
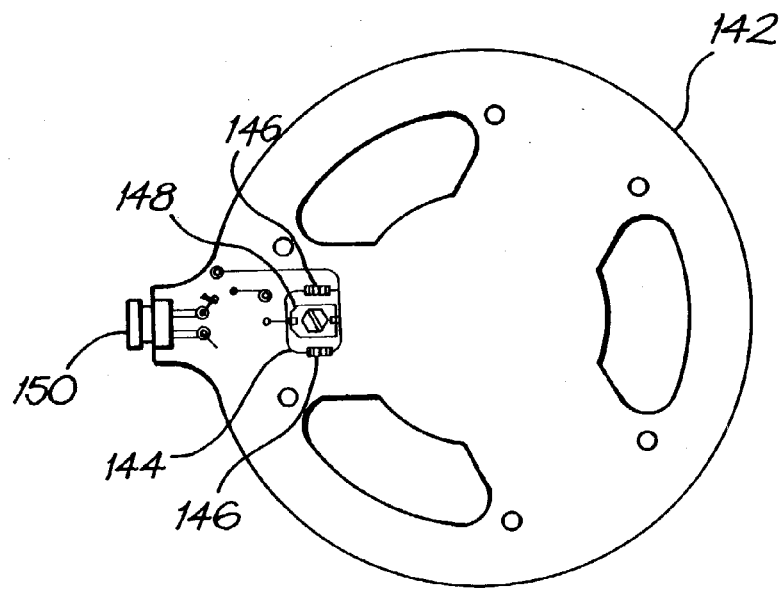
FIG. 11 shows a plan view of the transmission device.
Figure 12:
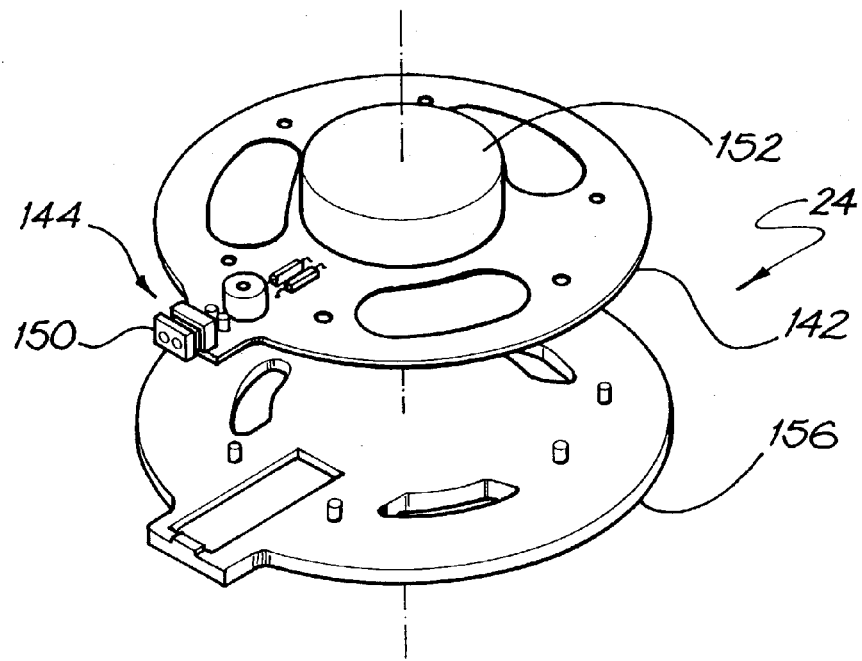
FIG. 12 shows a-three dimensional, exploded view of part of the transmission device.
Figure 13:
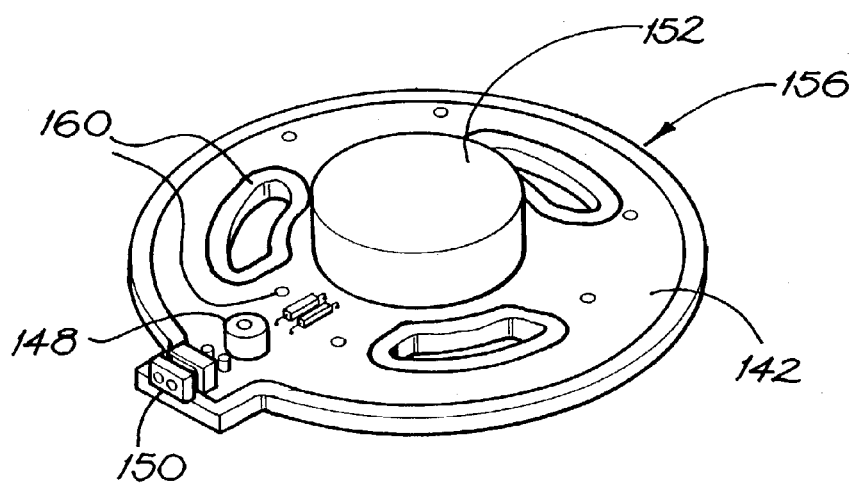
FIG. 13 shows a three dimensional view of the part of the transmission device of FIG. 11.

A sensor pack 26 is shown in greater detail in FIG. 9 of the drawings. The sensor pack 26 comprises a casing 180 made up of mating shells 182 and 184. The shells 182 and 184 enclose a printed circuit board (PCB) 186 carrying the electronic components.

A connector 188 is arranged at each end of the sensor pack 26. A conductor 190 is connected to each connector 188. The sensor packs 26 are, in use, mounted on the skin 58 of the patient's body and communicate with the controller 22.

Each sensor pack 26 makes use of a gyroscope and accelerometers for measuring angular velocity in at least one plane of motion, measuring acceleration components in three dimensions and measuring outputs from two pressure sensors and one strain gauge or three pressure sensors alone for determining positional information of the lower extremities 28, 30 and torso 32 of the patient's body 18. The data from the sensor packs 26 are fed via the controller interface 102 to the control device 100 of the controller 22. More particularly, each sensor pack 26 monitors angular velocity in the sagittal plane of a body segment on which that the particular sensor pack 26 is mounted. Further, the sensor pack 26 monitors linear acceleration experienced in three dimensions in relation to the body segment to which the sensor pack 26 is attached. Each sensor pack 26 also monitors the sagittal and coronal angle of its associated body segment.

It will be appreciated that, in respect of each of the lower extremities 28, 30, the relative positions of the thigh (the part of the lower extremity 28, 30 between the hip and knee) and the leg (the part of the lower extremity 28,30 between the knee and ankle) relative to each other and the torso 32 need to be monitored. Accordingly, each lower extremity 28, 30 uses at least two sensor packs 26, one mounted on the thigh and one mounted on the leg.

It is a particular advantage of the invention that a multi-purpose FES system 10 is provided making use of a single, multi-purpose stimulator 16. The system 10 thus provides recipients with the ability to control muscles which, as a result of spinal cord injury, are no longer under voluntary control. The benefits provided by the system 10 to the recipient include functional upright mobility, bladder, bowel and erection control, pressure relief, lower extremity exercise, enhanced quality of life, amongst other advantages.

Another advantage of the invention is that the stimulator 16 is implanted, together with subcutaneous implantation of the leads and electrodes 20, thereby inhibiting snagging and damaging of the implantable parts 12 of the system 10. This is also facilitated by providing the leads and electrodes 20 as separate leads to facilitate subcutaneous tunnelling insertion of such leads and electrodes 20.

A further advantage of the invention resides in the fact that the need for highly invasive non reversible surgical procedures such as rhizotomies is obviated.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A multi-purpose Functional Electrical Stimulation (FES) system comprising:
    a multi-function, implantable stimulator configured to stimulate at least one lower extremity site and at least one spinal cord site in a patient's body, the stimulator comprising:
    a control unit;
    a receiving device configured to send signals to the control unit;
    a plurality of bundles of electric leads connected to the control unit, each lead terminating in at least one electrode to provide a plurality of discrete groups of electrodes associated with each of the different sites, each group of electrodes being operable to stimulate its associated site in the patient's body, under the action of stimulation signals from the control unit; and
    a housing defining at least one suture opening for suturing the housing in position;
    a transmitter, arranged externally of the patient's body, configured to supply signals transcutaneously to the receiving device; and
    a controller in communication with the transmitter via a communications interface unit.

2. The system of claim 1 in which the stimulator is configured to effect stimulation in at least four sites of the patient's body.

3. The system of claim 2 in which the at least four sites include a posterior and anterior right lower extremity, a posterior and anterior left lower extremity, a posterior, sacral region of a spinal cord of the patient and at a conus of the patient's spinal cord.

4. The system of claim 1 in which the stimulator is implanted, in use, in a substantially central location in the patient's body, the stimulator being connected to the sites in the patient's body to be stimulated via the electrodes and their associated leads to deliver the appropriate stimulation to the desired sites by dedicated, application specific electrodes.

5. The system of claim 1 in which the electrodes are configured to be implanted in the patient's body by a surgical, subcutaneous tunneling technique to reduce the number and size of the incisions to be made to the patient's body.

6. The system of claim 1 in which the receiving device of the stimulator is in the form of an antenna.

7. The system of claim 6 in which the device is RF operable and is in the form of an RF receiver coil.

8. The system of claim 7 in which the transmitter is in the form of an RF transmitter coil arranged, in use, externally of the patient's body in register with the receiver coil so that RF signals are transmitted transcutaneously to the stimulator, in use.

9. The system of claim 8 in which the transmitter coil is removably arranged with respect to the stimulator.

10. The system of claim 9 in which the stimulator includes a retaining means for removably retaining the transmitter coil in position relative to the stimulator.

11. The system of claim 10 in which the retaining means is in the form of a magnet which cooperates with a complementary magnet carried by the transmitter coil so that the transmitter coil is held in position relative to the stimulator by magnetic attraction.

12. The system of claim 11 in which the controller communicates with the transmitter via an implant interface of the communications interface unit using a dedicated, RF transmission protocol.

13. The system of claim 12 in which the protocol also incorporates reception telemetry for receiving data from the stimulator.

14. The system of claim 13 in which the controller is in the form of a hand-held programmable device and the communications interface unit is a custom designed, dedicated communications interface unit.

15. The system of claim 12 in which the interface unit includes a peripherals interface for enabling the controller to communicate with peripheral devices.

16. The system of claim 15 in which the peripherals interface includes a microphone interface for enabling the patient to issue voice commands to the controller via a microphone connected to the microphone interface.

17. The system of claim 15 in which the peripherals interface includes a remote control interface.

18. The system of claim 15 in which the peripherals interface includes a sensor pack peripherals interface for effecting communication with sensor packs, each sensor pack being provided to sense orientation of the patient's torso and extremities when exercising of the patient's extremities is to be performed or when the patient wishes to execute a standing, stepping or sitting operation.

19. The system of claim 18 in which the controller receives data regarding the positioning of the patient's extremities via the sensor packs and the sensor pack peripherals interface.

20. The system of claim 1 which further includes an external skin surface stimulating device which effects external stimulation, as opposed to subcutaneous stimulation, of certain of the patient's muscles.

21. A multi-purpose Functional Electrical Stimulation (FES) system comprising:
a multi-function, implantable stimulator configured to stimulate at least one lower extremity site and at least one spinal cord site in a patient's body, the stimulator comprising:
a control unit;
a receiving device configured to send signals to the control unit;
a plurality of bundles of electric leads connected to the control unit, each lead terminating in at least one electrode to provide a plurality of discrete groups of electrodes associated with each of the different sites, each group of electrodes being operable to stimulate its associated site in the patient's body, under the action of stimulation signals from the control unit;
a transmitter, arranged externally of the patient's body, configured to supply signals transcutaneously to the receiving device; and
a controller in communication with the transmitter via a communications interface unit,
wherein the electrodes are configured to be implanted in the patient's body by a surgical, subcutaneous tunneling technique.

22. The system of claim 21, wherein the stimulator further comprises:
a housing of a bio-compatible material, said housing defining at least one suture opening for suturing the housing in position.

23. The system of claim 21 in which the stimulator is configured to effect stimulation in at least four sites of the patient's body.

24. The system of claim 21 in which the stimulator is implanted, in use, in a substantially central location in the patient's body, the stimulator being connected to the sites in the patient's body to be stimulated via the electrodes and their associated leads to deliver the appropriate stimulation to the desired sites by dedicated, application specific electrodes.

25. The system of claim 21 in which the transmitter is in the form of an RF transmitter coil arranged, in use, externally of the patient's body in register with the receiver coil so that RF signals are transmitted transcutaneously to the stimulator, in use.

26. A multi-purpose Functional Electrical Stimulation (FES) system comprising:
a multi-function, implantable stimulator configured to stimulate at least four different sites in a patient's body including a posterior and anterior right lower extremity, a posterior and anterior left lower extremity, a posterior, sacral region of a spinal cord of the patient and at a conus of the patient's spinal cord, the stimulator comprising:
a control unit;
a plurality of bundles of electric leads connected to the control unit, each lead terminating in at least one electrode to provide a plurality of discrete groups of electrodes associated with each of the at least different sites, each group of electrodes being operable to stimulate its associated site in the patient's body, under the action of stimulation signals from the control unit; and
an external controller in communication with the control unit via a transcutaneous communications link.

27. The system of claim 26 in which the stimulator is implanted, in use, in a substantially central location in the patient's body, the stimulator being connected to the sites in the patient's body to be stimulated via the electrodes and their associated leads to deliver the appropriate stimulation to the desired sites by dedicated, application specific electrodes.

28. The system of claim 26 in which the electrodes are configured to be implanted in the patient's body by a surgical, subcutaneous tunneling technique to reduce the number and size of the incisions to be made to the patient's body.

29. The system of claim 26 which further includes an external skin surface stimulating device which effects external stimulation, as opposed to subcutaneous stimulation, of certain of the patient's muscles.

30. The system of claim 26, wherein the stimulator further comprises:
a housing of a bio-compatible material, said housing defining at least one suture opening for suturing the housing in position.

* * * * *